(12) United States Patent
Yugari et al.

(10) Patent No.: US 8,801,697 B2
(45) Date of Patent: Aug. 12, 2014

(54) URINATION CONTROL DEVICE

(75) Inventors: Masazumi Yugari, Tokyo (JP); Hidenori Takagi, Chikuma (JP)

(73) Assignee: Cheiron Japan Co., Tokyo (JP)

( * ) Notice: Subject to any disclaimer, the term of this patent is extended or adjusted under 35 U.S.C. 154(b) by 0 days.

(21) Appl. No.: 13/265,286

(22) PCT Filed: Apr. 19, 2010

(86) PCT No.: PCT/JP2010/056915
§ 371 (c)(1), (2), (4) Date: Oct. 19, 2011

(87) PCT Pub. No.: WO2010/122976
PCT Pub. Date: Oct. 28, 2010

(65) Prior Publication Data
US 2012/0053570 A1  Mar. 1, 2012

(30) Foreign Application Priority Data
Apr. 20, 2009  (JP) ................ 2009-102363

(51) Int. Cl.
*A61M 27/00* (2006.01)
(52) U.S. Cl.
USPC ............... 604/544; 604/9; 604/247; 604/540; 251/65; 623/11.11; 623/23.64; 623/23.66; 600/29; 600/30; 600/31
(58) Field of Classification Search
None
See application file for complete search history.

(56) References Cited

U.S. PATENT DOCUMENTS

| 3,233,610 A | | 2/1966 | Wade et al. |
|---|---|---|---|
| 3,731,670 A | * | 5/1973 | Loe .................................. 600/30 |
| 4,865,588 A | | 9/1989 | Flinchbaugh |
| 4,942,098 A | * | 7/1990 | Hamamura et al. .......... 428/555 |
| 5,041,092 A | * | 8/1991 | Barwick ....................... 604/104 |
| 5,114,398 A | | 5/1992 | Trick et al. |
| 5,234,409 A | | 8/1993 | Goldberg et al. |
| 5,512,032 A | | 4/1996 | Kulisz et al. |

(Continued)

FOREIGN PATENT DOCUMENTS

| CN | 2043114 U | 8/1989 |
|---|---|---|
| EP | 1 072 238 A1 | 1/2001 |

(Continued)

OTHER PUBLICATIONS

Chinese Office Action dated Apr. 3, 2013.

(Continued)

*Primary Examiner* — Tan-Uyen T Ho
*Assistant Examiner* — Eric Bryant
(74) *Attorney, Agent, or Firm* — Arent Fox LLP

(57) ABSTRACT

A urination control device includes a conduit to be inserted into the urethra, an upstream restraint member located upstream of the conduit and having a through hole, a control member located on the downstream side from the upstream restraint member in the conduit, and a downstream restraint member located on the downstream side from the control member in the conduit, wherein the upper restraint member and control member attract each other with magnetic force, and the control member is brought in contact with the opening portion of the through hole in the upstream restraint member at least in the state exerting no fluid pressure on the upstream side so as to block passage of fluid through the upstream restraint member and admit the passage of fluid through the downstream restraint member in the state engaged with the control member.

10 Claims, 12 Drawing Sheets

(56) References Cited

U.S. PATENT DOCUMENTS

| | | | | |
|---|---|---|---|---|
| 5,624,374 | A | * | 4/1997 | Von Iderstein .................. 600/29 |
| 5,795,288 | A | * | 8/1998 | Cohen et al. .................... 600/29 |
| 6,066,088 | A | * | 5/2000 | Davis .............................. 600/29 |
| 6,234,956 | B1 | * | 5/2001 | He et al. .......................... 600/30 |
| 2002/0143318 | A1 | * | 10/2002 | Flinchbaugh ................ 604/544 |
| 2002/0165427 | A1 | * | 11/2002 | Yachia et al. ................... 600/31 |
| 2005/0187427 | A1 | * | 8/2005 | Connors et al. ................ 600/29 |
| 2006/0205997 | A1 | * | 9/2006 | Whalen et al. ................. 600/30 |
| 2006/0229553 | A1 | * | 10/2006 | Hammack et al. ......... 604/96.01 |
| 2007/0255222 | A1 | * | 11/2007 | Li et al. ......................... 604/174 |

FOREIGN PATENT DOCUMENTS

| | | | |
|---|---|---|---|
| EP | 1072238 | A1 | 1/2001 |
| JP | 3-118059 | A | 5/1991 |
| JP | 6-14950 | A | 1/1994 |
| JP | 7-204217 | A | 8/1995 |
| JP | 10-507652 | A | 7/1998 |
| JP | 11-504538 | A | 4/1999 |
| JP | 2004-523296 | A | 8/2002 |
| JP | 2002-536116 | A | 10/2002 |
| WO | WO 9603942 | A2 | 2/1996 |
| WO | WO 96/34587 | A1 | 11/1996 |
| WO | WO 00/02499 | | 1/2000 |
| WO | WO 00/02499 | A1 | 1/2000 |
| WO | WO 00/47141 | A1 | 8/2000 |
| WO | WO 02/065959 | A1 | 8/2002 |
| WO | WO 2006/115225 | A1 | 11/2006 |

OTHER PUBLICATIONS

European Search Report issued in EP Application No. 10767033.3, dated Dec. 6, 2012.

* cited by examiner (a)

(b)

(c)

(a)

(b)

(c)

(a)

(b)

(a)

(b)

(c)

(a)

(b)

URINATION CONTROL DEVICE

TECHNICAL FIELD

The present invention relates to a urination control device for preventing urinary incontinence.

BACKGROUND ART

The urinary incontinence is involuntary leakage of urine which can be proved objectively and defined as urinary leakage closely related to human life from social and hygiene perspectives (according to the International Incontinence Society). Now, the urinary incontinence is increasing specifically in men and women over 40 years old. Among types of urinary incontinence, stress urinary incontinence occurs most frequently and, supposedly, accounts for half or more of urinary incontinence in women. The stress urinary incontinence tends to involuntarily occur when experiencing abdominal pressure due to coughing, sneezing, lifting weights, walking for long time, singing, laughing or yelling, consequently resulting in causing suffering. Especially in women, the number of postmenopausal patients has markedly increased and it seems that the stress urinary incontinence is attributed to weakening of the pelvic floor muscle, which is caused by aging and occurs with greater frequency in women who have been pregnant or multiparous.

On the other hand, there is an overactive bladder which has drawn attention in recent years as another factor of urinary incontinence is a syndrome accompanied typically by frequent micturition or nocturia with urinary urgency as a predominant symptom and impending incontinence in certain instances, but overt causative disease thereof cannot be found in 12.4 percents of men and women aged 40 and over. (International Continence Society, 2002) This symptom has been reported to be increased with age and manifested in 20 percents of 70's and 35 percents of 80's. Also, the urinary incontinence associated with cystitis or interstitial cystitis is increasing.

Furthermore, the male-specific urinary incontinence may be developed due to disturbance of the bladder sphincter which occurs frequently in patients undergoing a total relaxation to treat prostate cancer or aftereffects suffered from indispensable dominant nerve section, aftereffects of radiation by radiotherapy for prostate cancer or prostate enlargement related surgery, or inadvertent nerve cutting happened during a surgery operation.

The group of diseases as a predominant symptom of urinary incontinence increases remarkably in male and female patients aged over 50 with igniting a social problem. A disturbance in pelvic floor muscle and flaccidity of a supporting structure such as a ligament are subjected to an operative procedure performed for the cure of female urinary incontinence on the basis of an integral theory.

However, a patient with less serious disease and a patient who prefers not to undergo surgery for any other reason have longed for ambisextrous-applicable measures capable of being relieved of physical pain by relatively-easy treatment without relying on any open surgery. As a passive way, there have been measures to absorb urine with a napkin or the like, collect urine in a urine-collecting bag worn on the penis or absorb urine with a pad or the like worn on the external genitals in case of precipitating urinary incontinence. However, these supplies must be replaced at frequent intervals and abhorrently cause unpleasant sensation and an objectionable odor in the event of attachment or replacement. Thus, there is a need for positive measures to control urination per se for preventing urinary incontinence. As an example, there have been devised a variety of methods using a device which is disposed in the urethra to prevent urinary leakage in its closed state and expedite urination in its casually open state.

Patent Literature 1 discloses a device provided in the urethra with a slit-type beaklike valve or a ball and a catheter with a valve for controlling urination of female. The device having a stylet to place a catheter in the urethra of woman is used to insert a urination tool from the body into the slit-type valve in the open state of the catheter valve, thereby enabling excretion of intravesical content.

Patent Literature 2 discloses a device comprising a bladder balloon to be fitted within the bladder, a conduit for conducting and excreting urinary flow, and an incontinence controller having an actuating valve for closing the conduit. The disclosed device is provided with a switching mechanism for operating the actuating valve by means of a spring and a manual actuating member so as to excrete urine by operating the actuating member to part a metallic valve head from the conduit and arbitrarily control incontinence by manually releasing the spring to close the conduit with the valve head.

Patent Literature 3 discloses a urination controlling device chiefly comprising a valve, which is disposed in the proximity of the bladder in the urethra. The disclosed device is used to control urination responsive to the abdominal muscle pressure with which a patient causes a muscle contraction by opening the valve with stress difference between the intravesical pressure in the bladder and the spring.

Patent Literature 4 discloses a urination controlling device comprising an intraductal coil to be inserted into the conduit and magnet-operated switching means so as to enable the switching operation of the switching means from outside. The device is intended to reliably perform closing of the urinary tract and controlling of urination.

In addition to the devices of the type set inside the body, there has been developed a device for controlling urination by arbitrarily dissolving a blocking medicament inserted in the urethra. Patent Literature 5 makes mention of inserting the medicament containing polyvinyl alcohol laced with alginate polymer or boronate polymer into the urethra to block the urethra, thereby to make a gel plug for preventing urinary incontinence. By infusing dextrose solution or the like into the gel plug when urinating, stability of gel is broken to dissolve the gel plug, consequently to allow urination.

CONVENTIONAL ART REFERENCES

Patent Literatures

Patent Literature 1: Japanese Unexamined Patent Publication No. 10-507652A,
Patent Literature 2: Japanese Unexamined Patent Publication No. 06-014950A,
Patent Literature 3: Japanese Unexamined Patent Publication No. 07-204217A,
Patent Literature 4: PCT International Patent Publication No. WO2006/115225, and
Patent Literature 5: Japanese Unexamined Patent Publication of PCT Application No. 2004-523296.

SUMMARY OF THE INVENTION

Problems to be Solved by the Invention

The techniques of these conventional known references lack reliability of control of urination and safety and comfort of the proposed devices, and therefore, cannot turn around QOL of a patient.

To be more specific, the device mentioned in Patent Literature 1 has a function of blocking liquid current with a slit-type valve and excreting urine by being inserted into the valve to open the valve. Thus, even when the device is not inserted, the slit-type valve to be closed with the intravesical pressure is not completely closed sometimes, consequently to make it difficult to completely prevent urinary incontinence by urination control difficult.

The device described in Patent Literature 2 is adapted for opening and closing the conduit with the metallic valve head, consequently to make it difficult to completely prevent urinary leakage difficult. In addition, the proposed device comprises a large number of parts for fixing the bladder balloon and complicated switching device, and therefore, is disadvantageously complicated in whole. Besides, the device employs many metal parts and complicated structure and configuration, consequently to possibly contaminate the urethra and injure the membrana mucosa.

Furthermore, the devices described in Patent Literatures 1 and 2 are developed for use by women, and therefore, can hardly be adapted in situ for men having long urethra.

The device described in Patent Literature 3 is complicated in structure and requires elaborate refinement for being placed in the urethra, consequently to possibly lead to problems of cost, reliability and stability of urination control and accuracy required for the urination control. Further, it seems to cause health problem due to a contamination in use, health problem due to adhesion of saprophytic bacteria relative to the contamination and lifetime problem of the device. Especially, there is concern that the complicated spring used for controlling the opening and closing in response to the intravesical pressure brings about contamination and difficulties of the sort and may largely affect the performance such as spring modulus changed due to degradation of constituent materials.

The device described in Patent Literature 4 has a high level of assuredness and stability, but employs a complicated mechanism comprising a switching means with a coil, so that improvement of device cost and accuracy has been much further required.

The technique proposed by Patent Literature 5 requires time and onerous labor for preparing gel material and requisite equipment, infusing the gel into the urethra and settling and solidifying the gel, since the proposed device makes a gel plug without placing any instrument inside the body. Thus, from this fact, impossibility of coping with suspected urge urinary incontinence can be predicted since it takes some time to close the urethra. Furthermore, the closing of the urethra with the gel plug has the problem of closing reliability specifically in case of high intravesical pressure.

The present invention was made in consideration of the aforementioned problems and it is an object of the invention to provide a urination control device capable of autonomous urination by adjusting the intravesical pressure with the abdominal pressure in starting the urination, thereby to prevent urinary incontinence.

Another object of the invention is to provide a urination control device capable of variously designing the intravesical pressure in opening and closing and gaining the stability and accuracy of the operation while ensuring the control of urination by secure closing and opening operation.

Still another object of the invention is to provide a urination control device capable of preventing infection and contamination by employing a simple structure and safe constituent materials and being applied to both men and women while improving QOL of the patients.

Means for Solving the Problems

To attain the objects described above according to the present invention, there is provided a urination control device described below.

The urination control device according to the present invention comprises a conduit to be inserted into the urethra, an upstream restraint member located upstream of the conduit and having a through hole, a control member located on the downstream side from the upstream restraint member in the conduit, and a downstream restraint member located on the downstream side from the control member in the conduit, wherein the upper restraint member and control member attract each other with magnetic force, the control member is brought in contact with the opening portion of the through hole in the upstream restraint member at least in the state exerting no fluid pressure (pressure of fluid, hydraulic pressure) on the upstream side so as to block passage of fluid through the upstream restraint member and admit the passage of fluid through the downstream restraint member in the state engaged with the control member.

This urination control device has the control member contacting with the opening of the through hole in the upstream restraint member by a magnetic force to block the passage of fluid through the upstream restraint member, thereby blocking the flow of urine in the conduit. Onto the upper part of the control member closing the opening, the intravesical pressure is exerted. When the contact is unsupportable with the magnetic force by increasing the intravesical pressure, the control member is released from the upstream restraint member to be retained while being pressed against the downstream restraint member by the intravesical pressure. The downstream restraint member admits the passage of fluid by releasing the blocking of the upstream restraint member, thereby permitting urination through the conduit. When the intravesical pressure is reduced by urination, the control member is again brought in contact with the opening of the through hole in the upstream restraint member by the action of the magnetic force against the intravesical pressure, thereby to close the conduit. The degree of power to close the derived by the magnetic force exerted on the upstream restraint member and control member, i.e. the intravesical pressure when opening the conduit, is controlled so as to adjust the intravesical pressure along of the distance between the control member and downstream restraint member when again closing the conduit.

In the urination control device of the invention, the control member is preferably made of a control spheric body having a diameter larger than the inner diameter of the through hole in the upstream restraint member formed in an annular shape. The control spheric body formed in a nearly true sphere can come into contact with the upstream restraint member in the same configuration in all directions. The control spheric body having the inner diameter larger than the annular upstream restraint member is attached to the upstream restraint member to close the upstream restraint member. Thus, the upstream restraint member is steadily closed by the control spheric body closely contacted therewith by the magnetic force without any means for closing the control member.

The urination control device of the invention further comprises a magnet, in which at least one part of the control member is preferably formed of magnetic material. The magnetic force of the magnet on the upstream acts to cause the control member formed of the magnetic material to be attracted toward the upstream restraint member. Since the control member has no magnetic pole, it is attracted to the upstream restraint member by the magnetic force of the magnet irrespective of the direction of location.

In the urination control device of the invention, the control member is preferably provided on its surface with a metallic film containing Au, Ag, Zn or Sn having a sterilization effect. The control member is liable to suffer adherence of bacteria or corrosion caused by exposure to excreta such as urine, so that the control member susceptible to deviation in engagement with upstream restraint member.

In the urination control device of the invention, the control member is preferably arranged so as to be parted from the upstream restraint member when the fluid pressure exerted on the upstream side of the control member is no less than a first value selected from the range of 25 to 200 cmH$_2$O and brought into contact with the upstream restraint member when the fluid pressure is no more than the aforesaid first value and no more than a second value selected from the range of 1.0 to 50 cmH$_2$O. By determining the first value of the fluid pressure, i.e. intravesical pressure, with which the control member is parted from the upstream restraint member to the upper limit of the abdominal pressure in daily living, leakage of urine can be prevented in daily living. By setting the second value at which the control member is in contact with the upstream restraint member to smaller than the first value, the conduit can be completely closed when reducing the urine pressure after urinating. Due to these actions, starting and stopping of urination can be controlled.

In the urination control device of the invention, the first value is preferably selected from the range of 100 to 180 cmH$_2$O. The intravesical pressure is rarely higher than the value in a variation range of daily living but readily exceeds it by exerting the abdominal pressure, so that the involuntary leakage of urine can be prevented in daily living, but urinating can be made at will by applying the abdominal pressure.

In the urination control device of the invention, the second value is preferably selected from the range of 20 to 30 cmH$_2$O. The conduit is promptly closed when decreasing the intravesical pressure as the result of urinating and after finishing urinating.

In the urination control device of the invention, it is preferable to disposed a support member with a deformation part made of shape-memory alloy having a transformation temperature lower than the temperature of the urinary bladder on the upstream side of the conduit so that the urination control device can be held in the urethra by spreading the support member in the urinary bladder. Since the deformation part is made of shape-memory alloy having the transformation temperature lower than the temperature of the urinary bladder, it is kept in its memorized steady shape and softly deforms at a temperature lower than the transformation temperature. Thus, in the state of stably placing the urination control device in the meatus urethra of the urinary bladder in the body, the support member maintains the memorized spread shape to prevent the urination control device from being left out from the urethra and be deformed and softened by change in temperature when attaching and detaching the device to facilitate attaching and detaching of the device without damaging the urinary bladder and urethral mucous membrane.

In the urination control device of the invention, it is preferable to attach a plurality of wing elements and form the deformation part in a linear shape along the wing elements, wherein the deformation part has a L-shaped axial cross-section at a temperature higher than the temperature of the urinary bladder to spread the wing elements of the support member in the urinary bladder. The wing elements of the support member are spread with the I-shaped deformation part at the temperature of the urinary bladder to hold the urination control device in the urinary bladder while preventing the device from being left out from the urethra.

In the urination control device of the invention, it is preferable to make the support member of the shape-memory alloy having a transformation temperature of 32° C. to 37° C. By determining the transformation temperature to a temperature slightly lower than the body temperature, the support member is reliably spread in its mounted state inside the body.

Effect of the Invention

According to the urination control device of the present invention, a patient can autonomously urinate in a state close to spontaneous urination without resorting manipulation conducted externally and using an instrument by adjusting fluid pressure exerted on the urination control device, i.e. the intravesical pressure with the abdominal pressure to control the urination. Hence, safety, accuracy and the controllability for reliably closing and opening can be ensured to prevent the urinary incontinence. The intravesical pressure in opening and closing a control valve can be variously designed to cope with the condition of the patient.

Further, the urination control device can be applied to both men and women and ensure the safety, accuracy and the controllability for reliably closing and opening since the device is simple in structure without using a spring or the like. With the simple structure, adulterants such as depositions to be evacuated into the urine are difficult to accumulate and contaminate, thereby to prevent infection and contamination by employing safe constituent materials and elements. Thus, this device is desirable for being embedded in the body while maintaining the QOL of the patients.

Furthermore, the device is simple in configuration and structure, saving on space and can be disposed near the urinary bladder through the urethra. That is, the device can easily be fitted in the meatus urethra, i.e. the bladder sphincter and detached therefrom without getting adverse effects, thereby to improve QOL of the patients.

The device of the invention makes it possible to control urination by voluntarily applying the abdominal pressure by a patient who has aftereffects from injury of the bladder sphincter or dominant nerve neurectomy, which are possibly caused frequently in an operation of radical prostatectomy for carcinoma prostata, or urinary incontinence or urethral hypermobility due to paralytic symptoms of the bladder sphincter, but is not serious enough to turn to an operative procedure or inoperable or undesirous of an operation for any reason. Furthermore, the device of the invention requires does not need a napkin or other supplies for urine absorption in preparation for urination, thus being unbothered by unpleasant sensation of usage and fetid odor. Due to these effects, the QOL of the patients can be improved.

BEST MODE FOR CARRYING OUT THE INVENTION

First Embodiment

Figure 1:
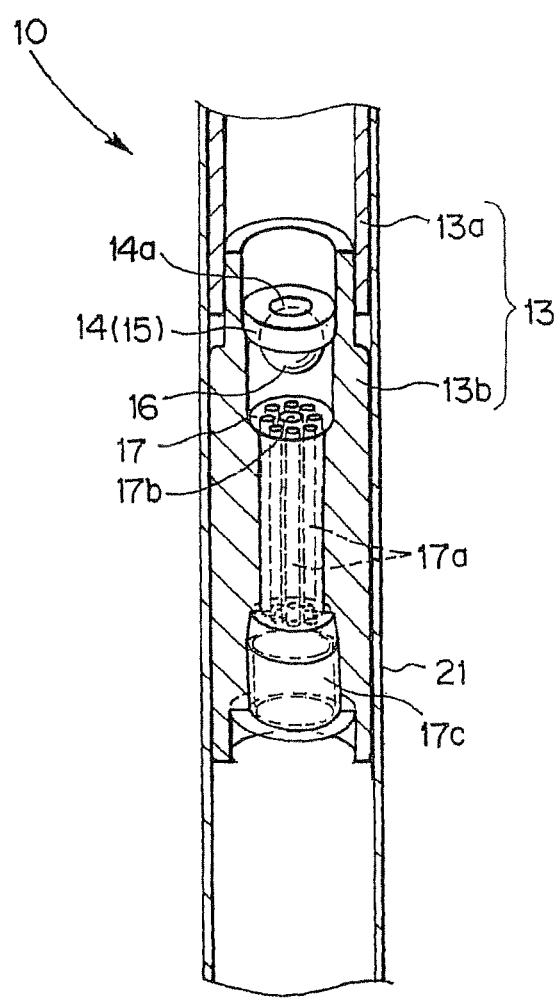
FIG. 1 is a partially broken perspective view showing the principal part of the urination control device according to a first embodiment of the present invention.
Figure 2:
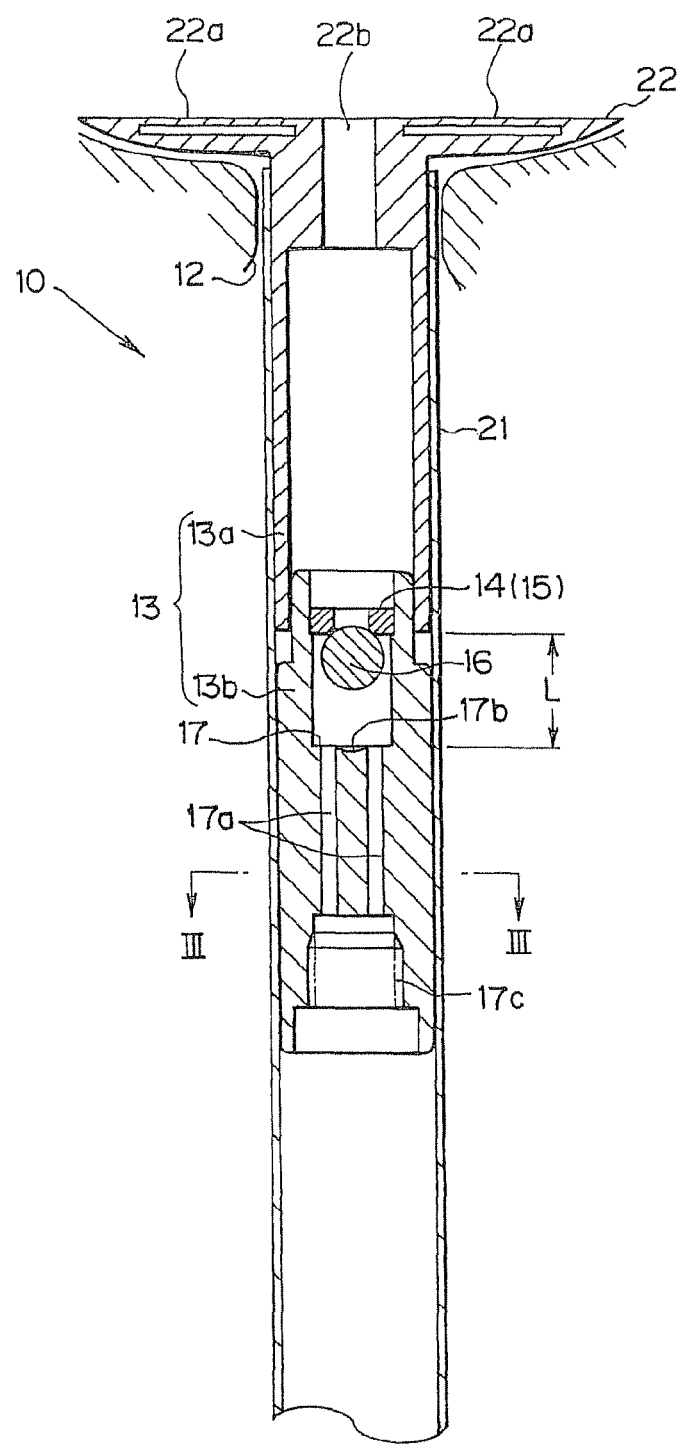
FIG. 2 is a sectional side view of the urination control device of FIG. 1.

FIG. 1 is a partially broken perspective view showing the principal part of the urination control device according to a first embodiment of the present invention, FIG. 2 is a sectional side view of the urination control device of FIG. 1, FIG. 3(a) is a cross sectional view taken along line III-III in FIG. 2, FIG. 3(b) is a plan view of a restrainer in the device of FIG. 2, and FIG. 3(c) is a front view showing a removing tool used in the first embodiment.

As shown in FIGS. 1 and 2, the urination control device 10 generally comprises a conduit 13 to be inserted into the urethra 12, an upstream restraint member 14 located upstream of the conduit 13, a control spheric body 16 serving as the control member of the present invention, which is located downstream of the upstream restraint member 14 in the conduit 13, and a downstream restraint member 17 located downstream of the control member in the conduit 13.

The conduit 13 is inserted into the urethra 12 and what is called a urinary catheter for urination. Although the diameter and length of the conduit 13 depends on the conditions of the urethra 12 of the patient and the situation of urination, but as a rough idea, there may be chosen 2 to 7 cm in length and 9 to 24 Fr (French), preferably, 16 to 24 Fr in outer diameter. As the constituent materials of the device, materials suitable for a catheter may be used, biocompatible, irrefrangible and hard-to-treat flexible plastic such as polyethylene, polypropylene and silicone resin is particularly desirable. The conduit 13 in this embodiment comprises an upstream member 13a and downstream member 13b. The upstream member 13a and downstream member 13b are both formed of flexible plastic by a monolithic molding method.

The upstream restraint member 14 and the control spheric body 16 are formed of magnetic material in whole or in part. In addition, the upstream restraint member 14 and the control spheric body 16 are mounted so as to magnetically attract each other. As well known, at least one part of the magnetic material turns to a magnet by magnetizing. The magnetic material is selectable from various sorts of metallic ferromagnet materials. The upstream restraint member 14 and/or the control spheric body 16 magnetically attract each other since at least one of the magnetic materials becomes a magnet having magnetic attraction force for attracting the other magnetic material by magnetizing. Meanwhile, it is desirable to form the control spheric body 16 of magnetic material by using the whole of the upstream restraint member 14 as the magnet 15 or providing one part thereof with the magnet 15. It is desirable to make only the control spheric body 16 to be magnetized so as to be attracted by the upstream restraint member 14 for easier contact anywhere on the spheric surface, rather than the control spheric body 16 provided with the magnet 15 having magnetic poles.

The upstream restraint member 14 is disposed on the inner wall of the conduit 13 and brought into fit contact with the control spheric body 16 for closing the urethra when not in urination. By increasing the fluid pressure exerted on the control spheric body 16 in urinating, the fit contact with the control spheric body 16 is released. Incidentally, the term "upstream" here means the upstream side in the urethra, i.e. the upstream side relative to the downward flow of urine in the urethra, which, in fact, points toward the direction close to the urinary bladder. The "fluid pressure" in this embodiment means the pressure of urine, which is exerted from the upstream on the urination control device 10 disposed in the urethra, i.e. urine hydraulic pressure or intravesical pressure.

The upstream restraint member 14 is formed in a disc-like or cylindrical annular shape. The upstream restraint member 14 is provided substantially in its central part with a circular through hole 14a. The circular through hole 14a is closed by coming the control spheric body 16 as described later in contact with the hole opening. When the through hole 14a is too small, the contact is easy to come off, thereby diminishing obstruction. On the contrary, when the through hole 14a is large, the area of contact between the upstream restraint member 14 and the control spheric body 16 is increased assuring the obstruction, but possibly developing a gap due to the too-large through hole. The size of the through hole 14a depends on the intravesical pressure (a fixed pressure value P1 as described later), which controls the urination, while it is desirable to determine 3.0 to 2.0 mm or less, particularly, 2.5 to 2.0 mm. The downstream-side end of the upstream restraint member 14 may be formed in a curve corresponding to the spheric surface of the control spheric body 16 so as to easily come in contact with the control spheric body 16. The upstream-side end of the upstream restraint member 14 may be formed in any shape.

One part of the conduit 13 may be formed as the major part of the upstream restraint member 14, or alternatively, another member different from the conduit 13 may be disposed within the conduit 13. The constituent material of the upstream restraint member 14 may be formed of metallic ferromagnet material, or may preferably be formed of polyethylene, polypropylene or other flexible plastics, more preferably, antibacterial plastics having high biocompatibility.

The major part of the upstream restraint member 14 in this embodiment is formed of an annular member integrated with the downstream member 13b such as of plastic. The upstream restraint member 14 is configured by embedding, in the major part, a single or plurality of magnets 15 each formed in an annular shape or other shape. The magnet 15 is a member having magnetic force such as a permanent magnet. For instance, a ring-shaped permanent magnet may be used directly as the upstream restraint member 14 to reduce the number of constituent parts of the device. The diameter of the upstream restraint member 14 in this embodiment is 3.5 to 5.5 mm, as an example.

The control spheric body 16 corresponds to the control member of the present invention. The control member serves to control the flow of urine by being contacted with or parted from the upstream restraint member 14 responsive to the intravesical pressure by the magnetic attractive force and the intravesical pressure exerted thereto. The control spheric body 16 is a member shaped in a nearly true sphere having a diameter larger than the inner diameter of the through hole 14*a* in the upstream restraint member 14, so as to bring one part of the spheric surface into fit contact with the upstream restraint member 14. The control spheric body 16 comes in contact with the opening of the through hole 14*a* in the upstream restraint member 14 by the magnetic force in the state of having no intravesical pressure on at least the upstream side, so that the passage of fluid through the upstream restraint member 14 can be blocked by fitting the spheric body into the opening. The diameter of the control spheric body 16 is larger than the diameter of the aforesaid through hole 14*a*, e.g. roughly 3.0 to 4.0 mm, while depending on the opening size of the through hole 14*a* and the intravesical pressure.

When the control spheric body 16 is not provided with the magnet 15, the control spheric body 16 may be entirely made of magnetic material magnetized. The constituent material of the control spheric body 16, there may be used metallic magnetic material such as stainless steel containing, for instance, iron and nickel. As one example, martensitic stainless steel having a strong magnetism and being resistant to corrosion is particularly preferable. By coating the metal with plastic, rubber, vinyl or the like, corrosion and dirt can be prevented without decreasing the magnetic force. For instance, there may be used a wholly soft ball formed by coating a metallic sphere with resin such as flexible plastic, e.g. a synthetic object made by combining a rubber ball with magnetic metal powder. The control spheric body 16 comes to be exposed to urine, making exfoliated cell residuum, salts such as calcium and bacilli easy to accumulate. The accumulation results in infection. Hence, it is also desirable to plate the metallic sphere of the control spheric body 16 with metal having a bacterial removal effect such as Au (gold), Ag (silver), Zn (zinc) and Sn (tin). The control spheric body 16 in this embodiment is composed of a flexible spheric body formed by coating a steel sphere with soft material and having a diameter of 3.0 to 4.0 mm.

The control spheric body 16 is arranged to bring the state of contacting with the upstream restraint member 14 to the state of coming out of the contact state when the fluid pressure applied to the upstream restraint member 14, i.e. the fluid pressure applied to the control spheric body 16 through the through hole 14*a* of the upstream restraint member 14, comes to a first value P1 or more. The first value P1 is determined by the magnetic strength of the magnet 15 and the structures of the control spheric body 16 and the upstream restraint member 14 such as the content, weight and size of magnetic material in the constituent materials, the distances between the constituent elements, and the size of the through hole 14*a* of the upstream restraint member 14. In this embodiment, the fluid pressure exerted on the control spheric body 16 in the installed state of the urination control device 10 corresponds to the intravesical pressure, and the first value P1 corresponds to the intravesical pressure in the range of preventing urination and is equivalent to a value in the value predictable from the abdominal pressure in daily living, as described later.

If the first value P1 is set to 100 to 180 $cmH_2O$ as a guide, preferably around 120 to 140 $cmH_2O$, urinary incontinence is not developed, while making autonomous urination possible because the intravesical pressure of a predetermined value or higher can easily be applied by consciously giving the abdominal pressure. The first value P1 in this embodiment is determined to P1=120 $cmH_2O$.

Figure 3:
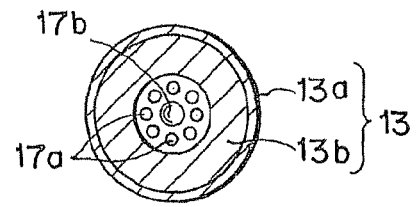
FIG. 3(a) is a cross sectional view taken along line in FIG. 2.
FIG. 3(b) is a plan view of a restrainer in the device of FIG. 2.
FIG. 3(c) is a front view showing a removing tool used in the first embodiment.
Figure 3:
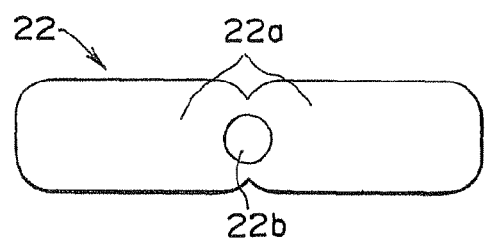
Figure 3:
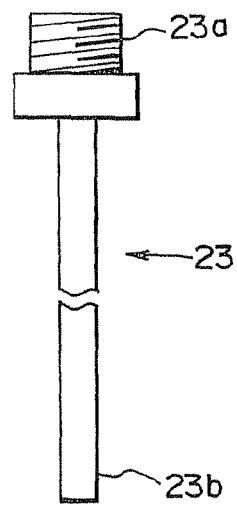

The downstream restraint member 17 is located on the urethra downstream side of the control spheric body 16 within the conduit 13. The downstream restraint member 17 is retained by exerting the urinary flow pressure during urination onto the control spheric body 16 coming off from the upstream restraint member 14 due to the intravesical pressure. The downstream restraint member 17 is formed of porous material, wire mesh material or the like so as to allow the flow of fluid in the state of retaining the control spheric body 16. The downstream restraint member 17 may be provided nearly at its center with a hole being substantially smaller than the diameter of the control spheric body 16 or a depression for easily holding the control spheric body 16. The downstream member 13*b* in this embodiment is closed at its downstream end to form a bottom 17*b* as shown in FIG. 3(*a*), and fluid pathway holes 17*a* are formed along the circumference of the bottom 17*b* which is the downstream restraint member 17. Since the downstream restraint member has the depression nearly in its center and the fluid pathway holes 17*a* smaller in diameter than the control spheric body 16, the fluid is allowed to pass therethrough in the state of retaining the control spheric body 16.

The positional relation among the downstream restraint member 17, control spheric body 16 and upstream restraint member 14 serves to bring the control spheric body 16 into contact with the upstream restraint member 14 when the fluid pressure applied to the upstream side of the control spheric body 16 becomes a second value P2 or lower. That is, when the intravesical pressure is over the second value P2, the control spheric body 16 comes in contact with the downstream restraint member 17, while the control spheric body 16 is attracted by the magnetic force of the magnet 15 to be separated from the downstream restraint member 17, and then, come in contact with the upstream restraint member 14. As the distance L between the upstream restraint member 14 and the downstream restraint member 17, the second value P2 of the pressure becomes small. This is because, even if the pressure exerted on the control spheric body 16 from the upstream side is low, the control spheric body 16 is hardly attracted in the direction toward the upstream restraint member in the case of the large distance L in the state of bringing the control spheric body 16 into contact with the downstream restrainer 17, since the magnetic force acting between the control spheric body 16 and the magnet 15 is inversely proportional to the distance L therebetween. Also, the magnetic strength acting between the control spheric body 16 and the magnet 15 depends on the second value P2 of the pressure. The second value P2 of the pressure is chosen from a value in the range of 1.0 to 50 $cmH_2O$, not exceeding the first value P1 at which the aforementioned upstream restraint member 14 and the control spheric body 16 are separated from each other, and that is the intravesical pressure when closing the urethra at the end of urination. The second value P2 is preferable 20 to 30 $cmH_2O$, and 25 $cmH_2O$ or lower in this embodiment.

As shown in FIG. 2, the urination control device 10 is provided on the upstream side of the urethra 12 of the conduit 13 with a diameter-reducible restrainer 22. The restrainer 22 is integrally formed with the flexible plastic upstream member 13*a* of the same material, which constitutes the upstream part of the conduit 13. The restrainer 22 in this embodiment has two wing elements 22*a* which expand auricularly in the horizontal direction from the conduit 13, as shown in FIG. 3(*b*). The wing members 22*a* are kept in its horizontally expanding state without application of force. The vicinity of the meatus urethra, in which the wing elements 22a are formed on the upstream side of the upstream member 13a, is made thick so as to maintain elasticity, and a urination passage 22b is formed there. When exerting a force in the direction of the central axis of the conduit 13, the wing elements 22a are folded with elasticity of the constituent materials of the upstream member 13a, so as to be carried in the outer diameter smaller than the diameter of a sheath 21 which will be described later.

The restrainer 22 desirably has an umbrella-shaped or mushroom-shaped lower surface in its expanded state so as to come in soft contact with the inner wall of the urinary bladder for preventing injury to the urinary bladder. By making the wing elements 22a thin and providing the through hole in its center, the wing elements 22a can be made soft in whole. Therefore, the wing elements 22a are easily bent to reduce the diameter of the restrainer 22 when attaching or detaching the device, without harming the urethra, as shown in FIG. 5(c). The restrainer 22 in the illustrated embodiment is formed of flexible plastic material, but the restrainer 22 may be made of metallic elastic wire or plate-like material with easy-to-bend properties such as stainless steel. Alternatively, the restrainer 22 may be made by radially connecting rod-like members through elastic bodies to be elastically contracted.

As shown in FIGS. 1, 2 and 5(a), on the lower end portion of the downstream member 13b of the conduit 13, there is disposed a removable part 17c for attaching and removing the conduit 13 from the ureter. The removable part 17c in this embodiment is made of a female screw capable of being entwisted into a male screw formed as an attaching/removing structure 23a of a removing tool 23 as described later.

The removing tool 23 for use in attaching and removing is made of flexible plastic and has the attaching/removing structure 23a which can come in screw contact with the removable part 17c. Separately from the screwing operation, the attaching/removing structure 23a of the removing tool 23 may be connected with the removable part 17c of the downstream member 13b by an intermeshing, holding or hooking method or some other ways.

The urination control device 10 is inserted into the sheath 21 before being set into the body. The sheath 21 is a tube of flexible plastic or metal, having a diameter somewhat larger than the outer diameter of the conduit 13. In the embodiment shown in FIG. 2, the sheath 21 has an inner diameter of 18 to 24 Fr and a length of 10 to 30 cm, and the conduit 13 has an outer diameter of 16 to 20 Fr and a length of 2 to 7 cm.

Incidentally, all the components noted above are set inside the body and is exposed to urine containing metabolite waste products, thereby easily causing dirt adhesion of exfoliated cells, microorganisms, inorganic matter such as calcium and urine sediment such as salts and/or rust on metallic parts. Thus, since these possibly cause much further contamination such as saprophyte thrives, it is desirable to make it difficult to cause these sorts of inconvenience. The surface should preferably be made smooth or coated to minimize the dirt adhesion or antimicrobially impregnated. As a coating agent for coating the subject elements, materials of the same nature as that used for a catheter, injection needle and stent may be applied. Alternatively, fluorine resin, Teflon (registered trade mark) and fluorocarbon may be used for surface treatment. The coating treatment is applicable for all the components including the inner and outer surface elements of the conduit 13, other parts constituting the device of the invention and parts coming in contact with urine. In addition to the coating treatment, the polymer surface may be lubricated to prevent dirt adhesion and contamination. Also, polymer having antimicrobial and antibacterial properties may be used. The components may be subjected to surface treatment with rust-free, bactericidal metal such as Au.

Figure 4:
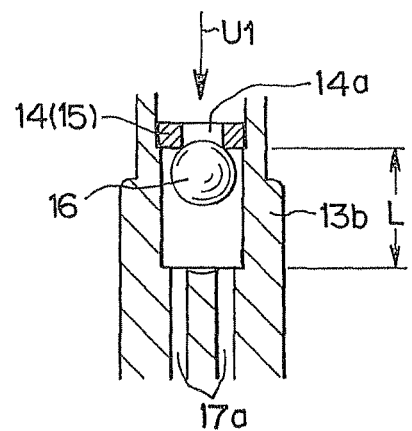
FIG. 4 is a sectional view of the principal part, showing the effect of the urination control device of FIG. 2.
Figure 4:
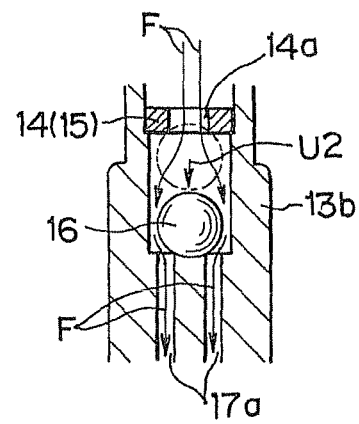
Figure 4:
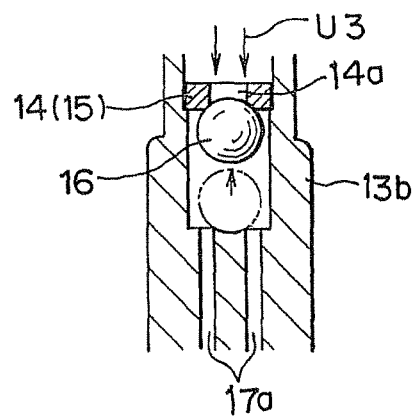

The operation of the urination control device 10 set inside the body will be described hereinafter. As shown in FIG. 4(a), the upstream restraint member 14 and the control spheric body 16 come in contact with each other by the magnetic attractive force acting between the magnet 15 and the control spheric body 16 when the intravesical pressure U1 is low. At this time, the conduit is blocked by closing the opening of the through hole 14a of the upstream restraint member 14 with the control spheric body 16. Since the upper portion of the control spheric body 16 closing the opening is exposed on the upstream side through the through hole 14a, the intravesical pressure U1 is exerted from the upstream.

The intravesical pressure U1 is increased as urine accumulates in the urinary bladder. When the intravesical pressure U1 comes to the aforementioned first value P1 or more, the control spheric body 16 is disengaged from the upstream restraint member 14 as shown in FIG. 4(b). The disengaged control spheric body 16 is pressed against the downstream restraint member 17 by the urinary flow pressure, coming in fit contact with the member 17. Even if the upstream restraint member 14 ceases closing and the control spheric body 16 is in contact with the downstream restraint member 17, the fluid pathway hole 17a allows a flow of fluid to cause urinary flow F through the through hole 14a and the fluid pathway hole 17a, thereby to make urination possible via the conduit 13.

The urinary flow pressure U2 is reduced with progression of the urination. As the flow pressure U2 of the urinary flow F is decreased to the aforementioned second value P2 or lower, the control spheric body 16 comes again in contact with the upstream restraint member 14 while the magnetic force acting between the control spheric body 16 and the magnet 15 resists the flow pressure U3, consequently to close the conduit 13, as shown in FIG. 4(c).

According to this formation, the intravesical pressures in opening and again closing when being decreased can be adequately adjusted by designing the intensity of the magnetic force produced by the magnet 15 and exerted on the control spheric body 16 and the distance L between the upstream restraint member 14 and the downstream restraint member 17. Further at the designing phase, the flow volume can be adjusted to cope with various patients with accordance with the size of the opening of the through hole 14a of the upstream restraint member 14, the size of the control spheric body 16 and the size and number of the through holes 17 of the downstream restraint member 17.

Since the adjustment can be made through design of the intravesical pressure in urinating, ease of urinating can be altered in accordance with the condition of the patient or as the other need arises. Moreover, since attaching and removing of the device can easily be carried out without any surgery, the device can be replaced and altered with ease.

Figure 5:
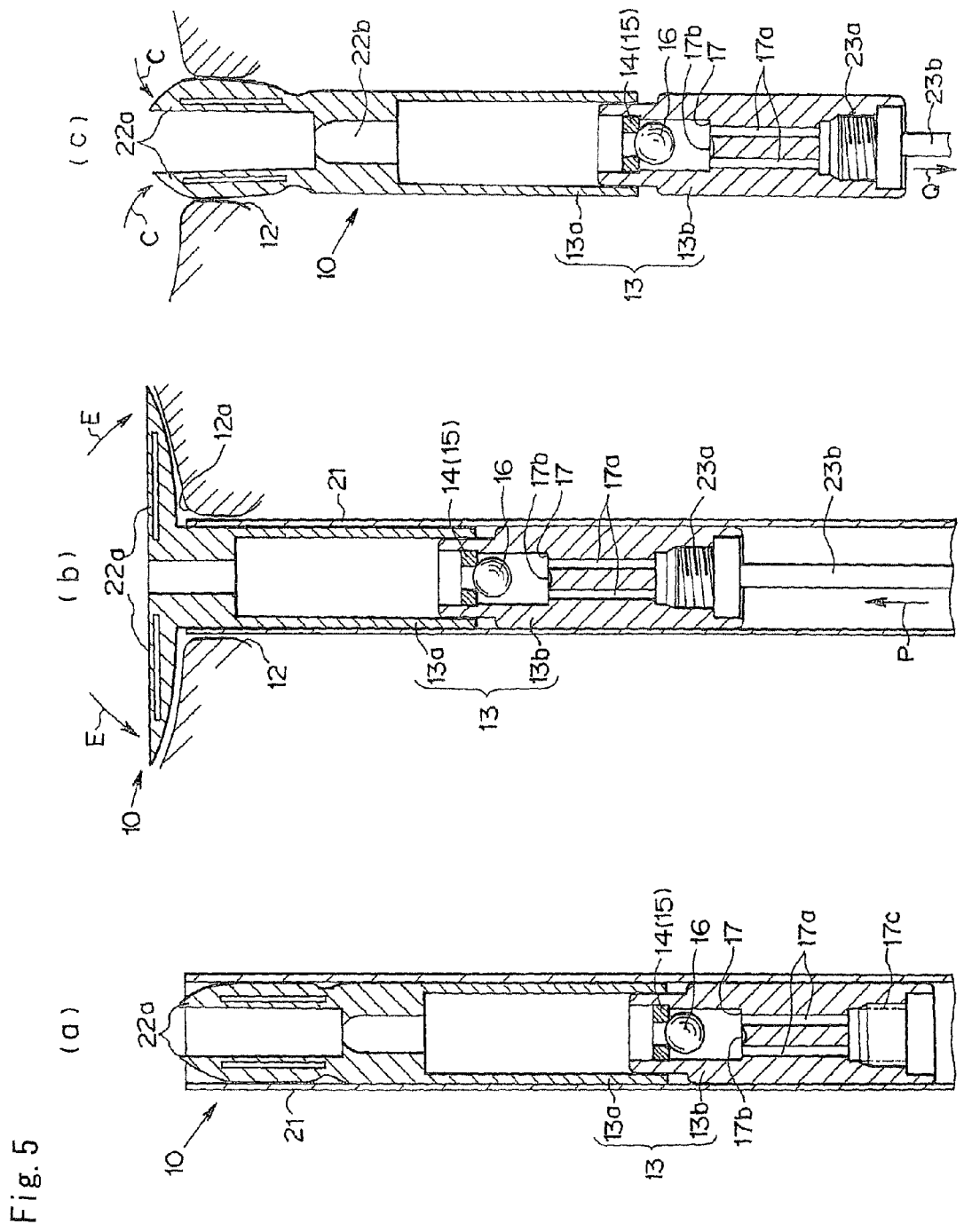
FIG. 5 is a sectional view of the principal part, showing the setting aspect of the urination control device of FIG. 2.

A method of setting the urination control device 10 according to this embodiment of the invention into the urethra will be described hereinafter with reference to FIG. 5. Before setting the device, the conduit 13 is in the state inserted into the sheath 21 and the restrainer 22 is inserted in the sheath 21 in the folded state as shown in FIG. 5(a). The sheath 21 is inserted into the urethra 12, and then, the conduit 13 is thrust in the pushing direction P to be inserted in the urinary bladder as shown in FIG. 5(b). At this time, it may be forcibly inserted by using a rod portion formed on the opposite side of the attaching/removing structure 23a of the removing tool 23 as a push rod 23b or with an elongated tool which is particularly alien to the removable part 17c, as one example. When the upper end of the conduit 13 advances close to the meatus urethra 12a of the urinary bladder, which is the bladder sphincter, the restrainer 22 is elastically spread in the opening direction E, thereby to be stably positioned in the urinary bladder. Hence, the device can be held easily and safely in position without harming the urinary bladder and the urethra of the patient. The sheath 21 is pulled out to be removed after setting the urination control device 10 in position.

Next, a method of removing the urination control device 10 in this embodiment from the urethra will be described. When removing the urination control device 10, the attaching/removing structure 23a of the removing tool 23 is connected with the removable part 17c of the downstream member 13b to pull out the urination control device 10 in the removing direction Q on the downstream. In an example shown in FIG. 5, the male screw of the attaching/removing structure 23a is entwisted into the female screw of the removable part 17c to pull out the device. The restrainer 22 is constricted in the closing direction C by being strongly pulled, resulting in being set in position in the diameter no more than the inner diameter of the urethra 12. Subsequently, the conduit 13 is pulled out from the urethra 12. At this time, the meatus urethra 12a of the urinary bladder and the urethra 12 are not hurt because of the flexibility of restrainer 22. Thus, the removal can easily without any harm to the urinary bladder and the urethra of the patient. Further safety can be ensured by inserting the sheath 21 into the urethra 12, connecting the removing tool 23 with the removable part 17c, thrusting the sheath 21 in the bladder lumen, pulling out the removing tool 23 to bring the entire restrainer 22 within the sheath 21 and then removing the sheath 21.

Second Embodiment

Figure 6:
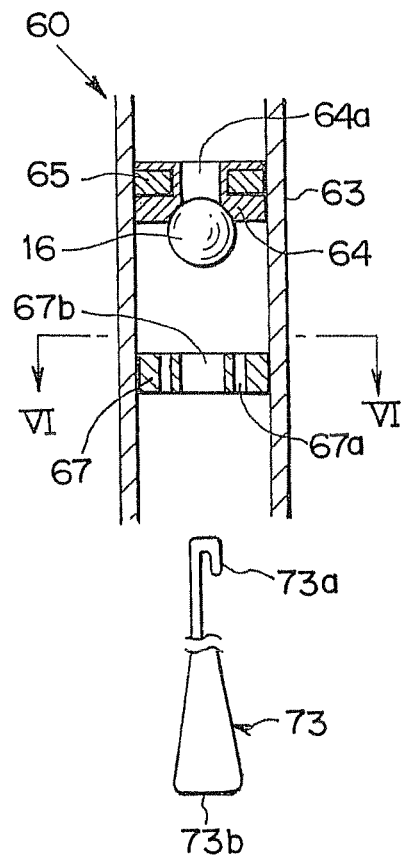
FIG. 6(a) is a sectional view of the principal part of the urination control device according to a second embodiment of the invention.
FIG. 6(b) is a sectional view taken along line VI-VI in FIG. 6(a).
Figure 6:
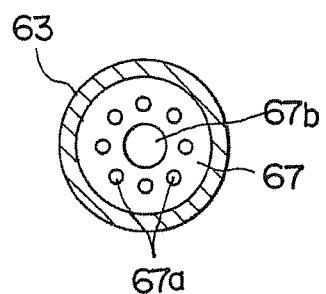

FIG. 6(a) is a sectional view of the principal part of the urination control device according to the second embodiment of the invention, and FIG. 6(b) is a sectional view taken along line VI-VI in FIG. 6(a). The elements indicated by like reference symbols with respect to those of the first embodiment have analogous structures and functions to the urination control device 10 of the first embodiment and will not be described in detail again.

In the urination control device 60 in this embodiment comprises a conduit 63 formed of one part of a flexible plastic tube, in which an upstream restraint member 64 and downstream restraint member 67 are assembled by welding or concaves/convexs couple means.

The upstream restraint member 64 is made of flexible plastic as with the conduit 63 and formed in a annular shape having a round through hole 64a in its substantial center. A magnet 65 is embedded in the flexible plastic body. The circumferential periphery of the opening of the through hole 64a in the surface on the downstream side has a curved surface substantially in match with the surface of the control spheric body 16 so as to come in ready contact with the spherical surface of the control spheric body 16.

The magnet 65 is embedded in the upstream restraint member 64 with adjusted distance from the surface on the downstream side of the upstream restraint member so as to exert magnetic force sufficient for supporting the control spheric body 16. This embodiment employs two rectangular permanent magnets opposite to each other along the circumference of the upstream restraint member 64. Meanwhile, even if three or more permanent magnets are disposed or a ring-shaped permanent magnet is embedded along the circumference, the permanent magnet may be barely formed on the upstream side and/or the downstream side.

The downstream restraint member 67 comprises an engaging hole 67b coming in engagement with the control spheric body 16 and a fluid pathway hole 67a for allowing passage of fluid in the engaged state. The downstream restraint member is made of a disc-like flexible plastic. Particularly in this embodiment, the downstream restraint member 67 and the conduit 63 are integrally molded in one body. The engaging hole 67b has a larger inner diameter than the diameter of the control spheric body 16 so that the control spheric body 16 can come in fit engagement with the engaging hole 67b when the intravesical pressure is exerted from the upstream.

When allowing the urination control device 60 to be attached into or removed from the urethra, a removing tool 73 shown in FIG. 6(b) is used. The removing tool 73 has an ancyroid attaching/removing structure 73a at its leading end. The urination control device 60 can be removed by passing the leading end of the removing tool 73 through the engaging hole 67b and pulling out the urination control device 60 with the ancyroid attaching/removing structure 73a hooked on the engaging hole 67b. The removing tool 73 in this embodiment has the rear end 73b somewhat larger in diameter than the engaging hole 67b, so that the downstream restraint member 67 can be thrust with the rear end 73b in setting the urination control device 60.

The magnet 65 in this embodiment is embedded as a separate part different from the upstream restraint member 64 and can be made of a permanent magnet in various forms in shape, size and number. Since the magnet is not barely formed, it is not exposed to the urinary flow, thereby to reduce deterioration. Because the upstream restraint member 64 is not a magnet but made of plastic, it can easily be processed and brought into contact with the control spheric body 16 and serve to block the urinary flow with ease. The downstream restraint member 67 has a simple configuration, thereby to facilitate processing. Besides, the urination control device 60 can easily be attached and removed.

Third Embodiment

Figure 7:
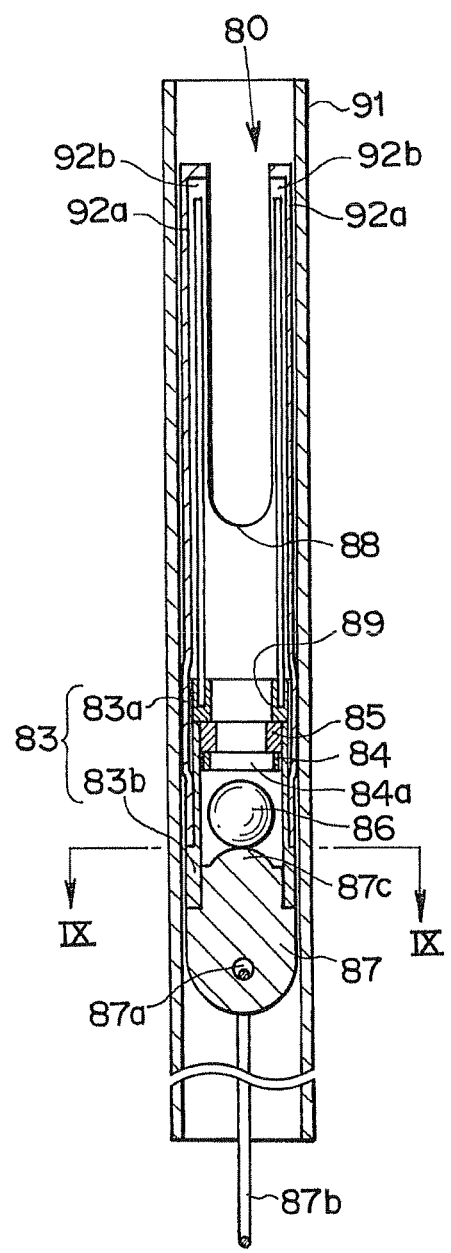
FIG. 7 is a sectional side view of the principal part of the urination control device according to a third embodiment of the present invention.
Figure 8:
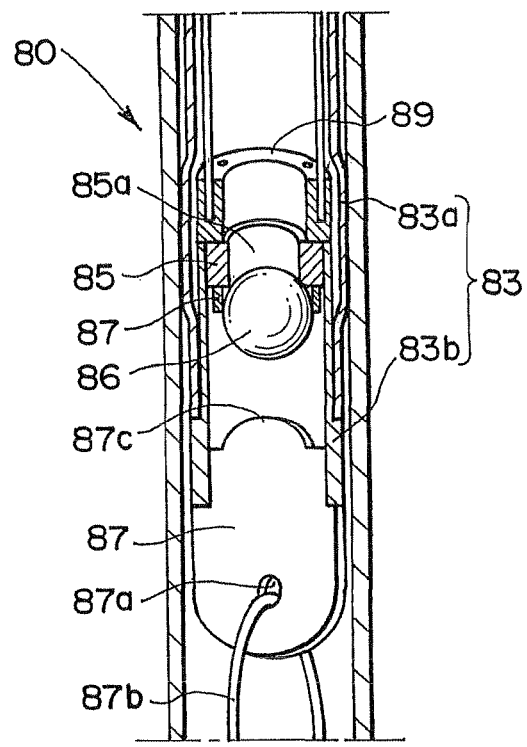
FIG. 8 is a partially broken perspective view of the principal part of the urination control device of FIG. 7.
Figure 9:
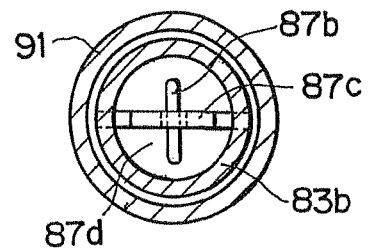
FIG. 9 is a cross sectional view taken along line IX-IX in FIG. 7.
Figure 10:
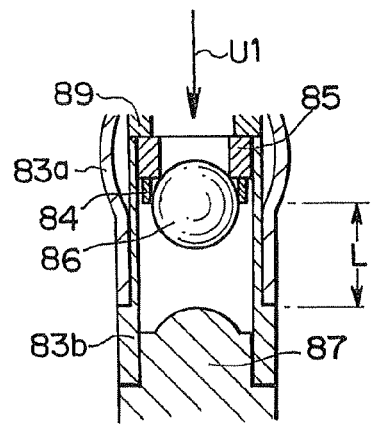
FIG. 10 is a sectional view of the principal part, showing the effect of the urination control device of FIG. 7.
Figure 10:
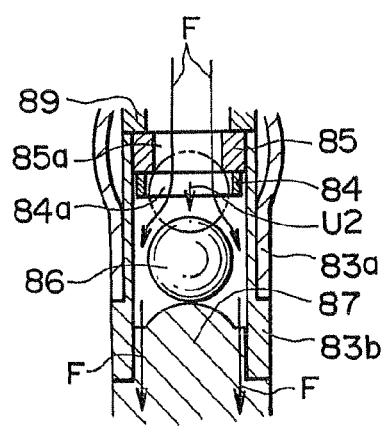
Figure 10:
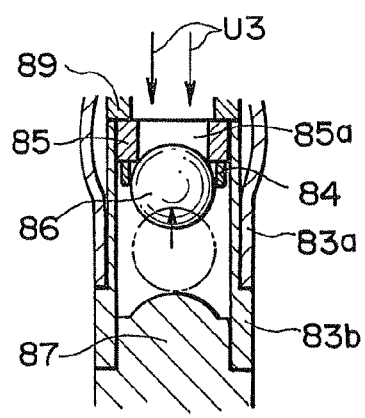
Figure 11:
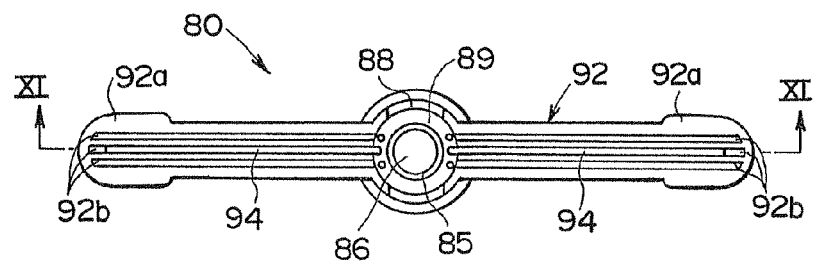
FIG. 11(a) is a plan view showing the restrainer in the spread state of the urination control device of FIG. 7.
FIG. 11(b) is a cross sectional view taken along line XI-XI in FIG. 11(a).
Figure 11:
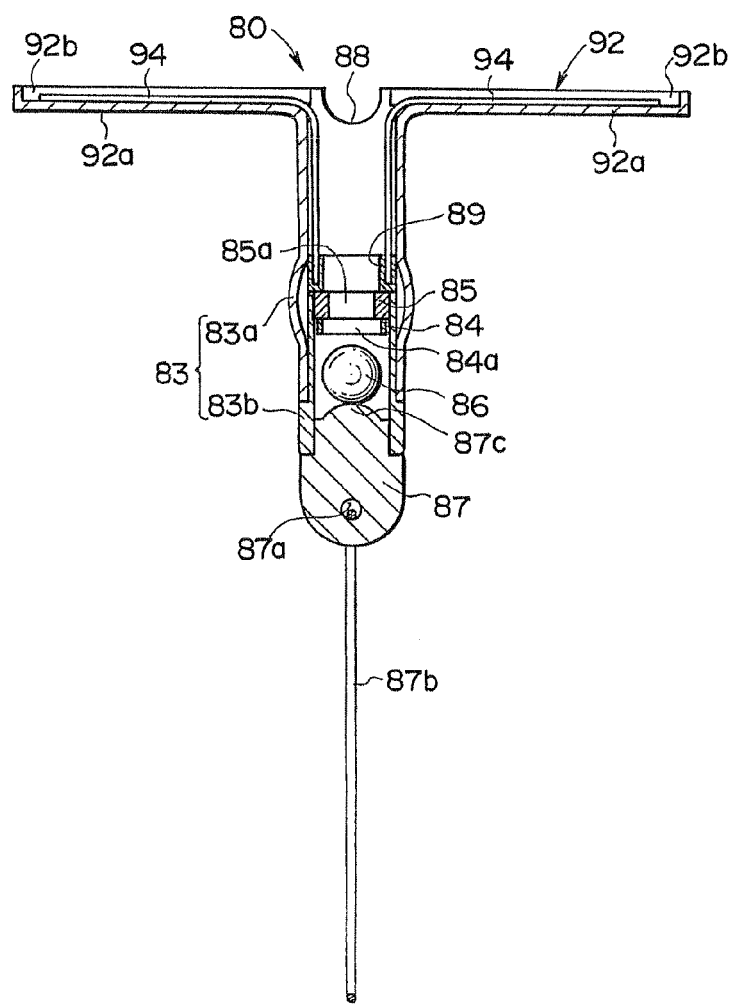
Figure 12:
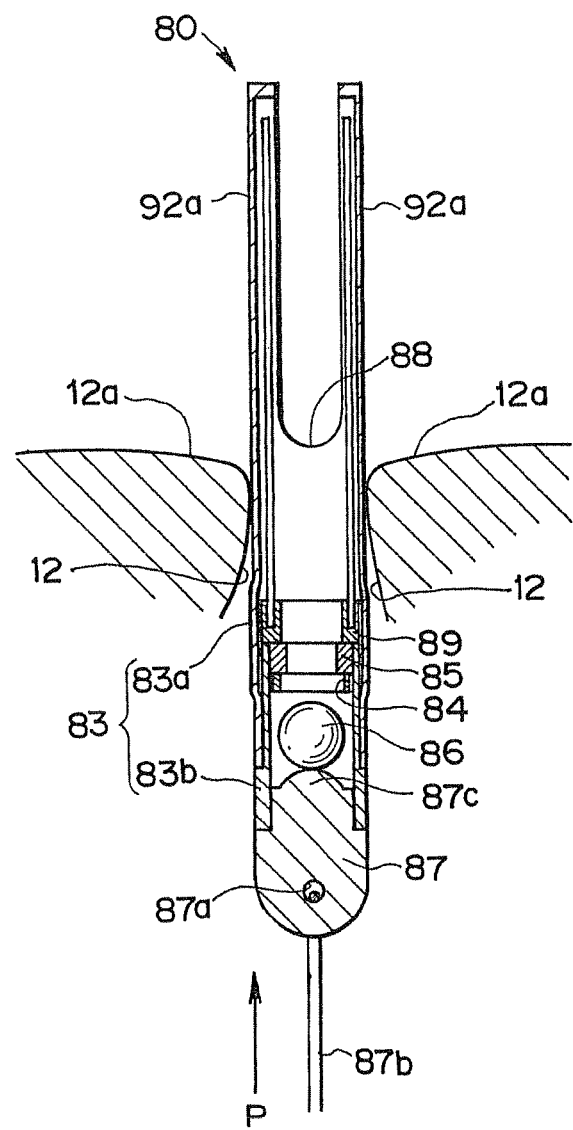
FIG. 12 is a sectional view of the principal part, showing the setting aspect of the urination control device of FIG. 7.
Figure 13:
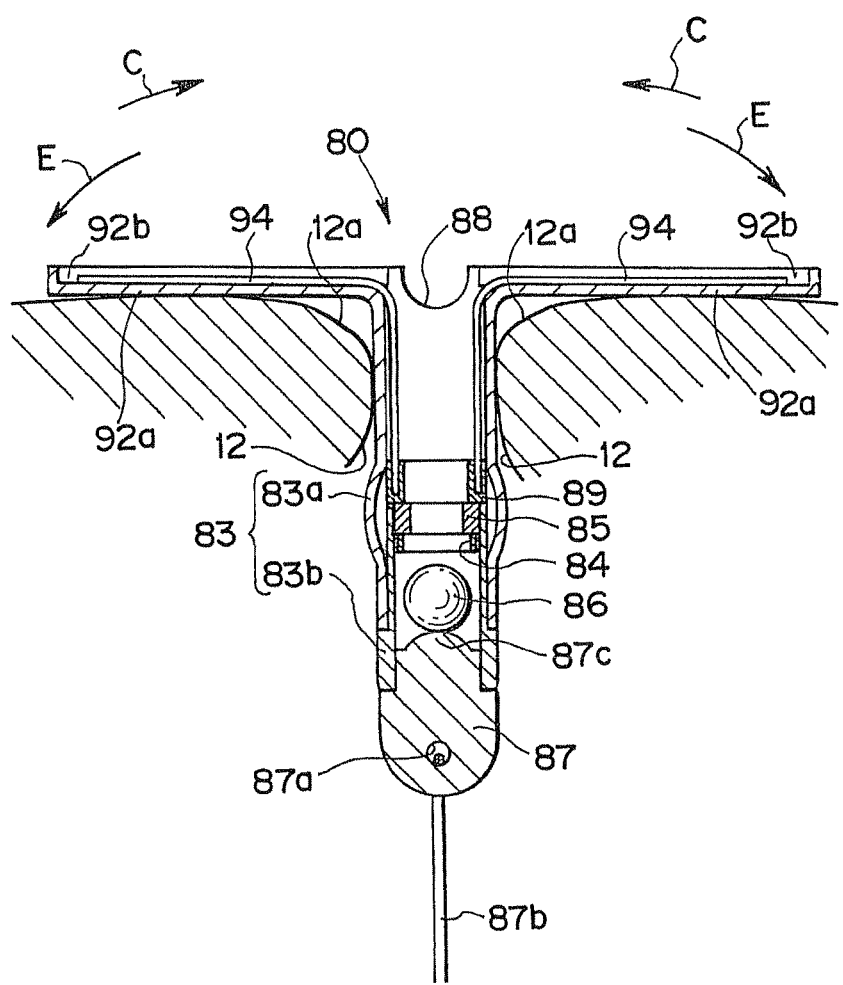
FIG. 13 is a plan view showing the restraint member in the spread state of the urination control device of FIG. 12.

FIG. 7 is a sectional side view of the principal part of the urination control device according to the third embodiment of the present invention; FIG. 8 is a partially broken perspective view of the principal part of the urination control device of FIG. 7; FIG. 9 is a cross sectional view taken along line IX-IX in FIG. 7; FIG. 10 is a sectional view of the principal part, showing the effect of the urination control device of FIG. 7; FIG. 11(a) is a plan view showing the restrainer in the spread state of the urination control device of FIG. 7, and FIG. 11(b) is a cross sectional view taken along line XI-XI in FIG. 11(a), FIG. 12 is a sectional view of the principal part, showing the setting aspect of the urination control device of FIG. 7; and FIG. 13 is a plan view showing the restraint member in the spread state of the urination control device of FIG. 12.

As shown in FIG. 7 and FIG. 8, the urination control device 80 has a conduit 83 being inserted into the urethra, and a restrainer 92 corresponding to the support member, which is disposed on the upstream side of the conduit with respect to the urethra. The restrainer is provided with a deformation part 94 made of shape-memory alloy.

The conduit 83 is inserted into the urethra 12 and what is called a urinary catheter for urination. Although the diameter and length of the conduit 83 depends on the conditions of the urethra 12 of the patient and the situation of urination, but as a rough idea, there may be chosen 2 to 7 cm in length and 9 to 24 Fr (French), preferably, 16 to 24 Fr in outer diameter. As the constituent materials of the device, materials suitable for a catheter may be used, biocompatible, irrefrangible and hard-to-treat flexible plastic such as polyethylene, polypropylene and silicone resin is particularly desirable.

The conduit 83 in this embodiment generally comprises an upstream restraint member 83a and a downstream restraint member 83b. The upstream member 83a is made of silicon rubber and provided on its upper portion with a restrainer 92 integrally molded therewith.

The upstream restraint member 84 and the control spheric body 86 are formed of magnetic material in whole or in part. In addition, the upstream restraint member 84 and the control spheric body 86 are mounted so as to magnetically attract each other. As well known, at least one part of the magnetic material turns to a magnet by magnetizing. The magnetic material is selectable from various sorts of metallic ferromagnet materials. The upstream restraint member 84 and/or the control spheric body 86 magnetically attract each other since at least one of the magnetic materials becomes a magnet having magnetic attraction force for attracting the other magnetic material by magnetizing. Meanwhile, it is desirable to form the control spheric body 86 of magnetic material by using the whole of the upstream restraint member 84 as the magnet 85 or providing one part thereof with the magnet 85. It is desirable to make only the control spheric body 86 to be magnetized so as to be attracted by the upstream restraint member 84 for easier contact anywhere on the spheric surface, rather than the control spheric body 86 provided with the magnet 85 having magnetic poles.

The upstream restraint member 84 is disposed on the inner wall of the conduit 83 and brought into fit contact with the control spheric body 86 for closing the urethra when not in urination. By increasing the fluid pressure in urinating, the fit contact with the control spheric body 86 is released. Incidentally, the term "upstream" here means the upstream side in the urethra, i.e. the upstream side relative to the downward flow of urine in the urethra, which, in fact, points toward the direction close to the urinary bladder. The "fluid pressure" in this embodiment means the pressure of urine, which is exerted from the upstream on the urination control device 10 disposed in the urethra, i.e. intravesical pressure. The upstream restraint member 84 is formed in a disc-like or cylindrical annular shape. The upstream restraint member 84 is provided substantially in its central part with a circular through hole 84a. The circular through hole 84a is closed by coming the control spheric body 86 as described later in contact with the hole opening. When the through hole 84a is too small, the contact is easy to come off, thereby diminishing obstruction. On the contrary, when the through hole 84a is large, the area of contact between the upstream restraint member 84 and the control spheric body 86 is increased assuring the obstruction, but possibly developing a gap due to the too-large through hole. The size of the through hole 84a depends on the intravesical pressure (a fixed pressure value P1 as described later), which controls the urination, while it is desirable to determine 3.5 mm or less, particularly, 3.0 mm or less. The downstream-side end of the upstream restraint member 84 may be formed in a curve corresponding to the spheric surface of the control spheric body 86 so as to easily come in contact with the control spheric body 86. The upstream-side end of the upstream restraint member 84 may be formed in any shape. The constituent material of the upstream restraint member 84 may be formed of metallic ferromagnet material, or may preferably be formed of polyethylene, polypropylene or other flexible plastics, more preferably, antibacterial plastics having high biocompatibility.

The upstream restraint member 84 is made of silicon rubber and provided at its center with a through hole 84a. The through hole 84a has an inner diameter of 2.0 to 3.0 mm and the upstream restraint member 84 has a thickness of 1.5 mm or less. The magnet 85 is disposed on the upstream of the upstream restraint member 84. The magnet 85 has a round through hole 85a, embedded in the upper end of the downstream restraint member 83b and caught between an intrusion portion 89 at the lower end of the upstream member 83a and the annular-shaped upstream restraint member 84 embedded in the downstream member 83b.

The control spheric body 86 corresponds to the control member of the present invention. The control member serves to control the flow of urine by being contacted with or parted from the upstream restraint member 84 responsive to the intravesical pressure by the magnetic attractive force and the intravesical pressure exerted thereto. The control spheric body 86 is a member shaped in a nearly true sphere having a diameter larger than the inner diameter of the through hole 84a in the upstream restraint member 84, so as to bring one part of the spheric surface into fit contact with the upstream restraint member 84. The control spheric body 86 comes in contact with the opening of the through hole 84a in the upstream restraint member 84 by the magnetic force in the state of having no intravesical pressure on at least the upstream side, so that the passage of fluid through the upstream restraint member 84 can be blocked by fitting the spheric body into the opening. The diameter of the control spheric body 86 is larger than those of the aforesaid through holes 84a and 85a and 5.0 mm or less, while depending on the opening size of the through hole 84a and the intravesical pressure. Only as a guide, the range of 2.0 to 3.0 mm is desirable.

The control spheric body 86 is arranged to bring the state of contacting with the upstream restraint member 84 to the state of coming out of the contact state when the fluid pressure applied to the upstream restraint member 84, i.e. the pressure applied to the control spheric body 86 through the through hole 84a of the upstream restraint member 84, comes to a first value P1 or more. The first value P1 is determined by the magnetic strength of the magnet 85 and the structures of the control spheric body 86 and the upstream restraint member 84 such as the content, weight and size of magnetic material in the constituent materials, the distances between the constituent elements, and the size of the through hole 84a of the upstream restraint member 84. The first value P1 corresponds to the intravesical pressure in the range of preventing urination and is equivalent to a value in the value predictable from the abdominal pressure in daily living, as described later.

In this embodiment, the control spheric body 86 is a flexible spheric body formed by plating a steel sphere with metal containing Au, Ag, Zn or Sn, having a sterilization effect.

When the fluid pressure applied to the upstream restraint member 86 via the through hole 84a of the upstream restraint member 84 and the through hole 85a of the magnet comes to a first value P1 or more, the contact state is released. The first value P1 corresponds to the intravesical pressure in the range of preventing urination and is equivalent to a value in the value predictable from the abdominal pressure in daily living, i.e. 25 to 200 $cmH_2O$.

The urination control is required to be responsive to the intravesical pressure including load predicted from the intravesical pressure and abdominal pressure in daily living. Although physiology of urination remains poorly understood, the intravesical pressure is generally kept low until specific amount of urine is accumulated in the urinary bladder in accordance with Laplace law. The intravesical pressure is increased by a variety of factors such as loud vocalization, laughing, coughing and sternutation. This being the case, it is thought that leakage of urine is caused by faulty closing of the bladder sphincter due to any disorder or aftereffects even when retention of the urine in the urinary bladder is decreased, while a healthy individual who can control closing of the bladder sphincter does not leak urine. Therefore, it is possible to prevent the urinary leakage by configuring appropriate settings so as to cope with the load when the intravesical pressure increases due to the ordinary factors of life as described above. The intravesical pressure can be predicted in the range of 25 to 200 cmH$_2$O. As a rough idea, it is 25 cmH$_2$O in a normal individual at ordinary times, and even when pressurization occurs due to common causes such as coughing, loud vocalization and various shocks, the intravesical pressure is rarely exceed 100 to 120 cmH$_2$O. Therefore, urinary incontinence is not caused as long as the intravesical pressure is set to 100 to 180 cmH$_2$O, preferably about 120 to 140 cmH$_2$O based on the aforementioned first value P1 as a measure for pressure. Also, autonomous urination is made possible because the intravesical pressure can easily be kept at not less than the prescribed value by consciously increasing the abdominal pressure. The first value P1 in this embodiment is determined to (P1=120 cmH$_2$O).

The downstream restraint member 87 is located on the urethra downstream side of the control spheric body 86 within the conduit 83. The downstream restraint member 87 is retained by exerting the urinary flow pressure during urination onto the control spheric body 86 coming off from the upstream restraint member 84 due to the intravesical pressure. The downstream restraint member 87 is formed of porous material, wire mesh material or the like so as to allow the flow of fluid in the state of retaining the control spheric body 86. The downstream restraint member 87 may be provided nearly at its center with a hole being substantially smaller than the diameter of the control spheric body 86 or a depression for easily holding the control spheric body 86.

In this embodiment, the downstream member 83b constituting the downstream part of the conduit 83 is made of acrylic material and integrally molded with the downstream restraint member 87 at the downstream member 83b. The downstream restraint member 87 is provided at its upper end with a protrusion 87c. As shown in FIG. 8 and FIG. 9, the downstream restraint member 87 is made of a plate having a thickness smaller than the diameter of the conduit 83 so as to admit passage of fluid from the upstream side via the fluid pathway hole 87d spaced between itself and the downstream member 83d. The diameter of the control spheric body 86 and the thickness of the downstream restraint member 83 are adjusted so as to prevent passage of the control spheric body 86 through the fluid pathway hole 87d. The downstream restraint member 87 is provided with a threading hole 87a through which a retaining thread 87b is passed for retaining the conduit 83 on the urethral sphincter of the urethra 12. The retaining thread 87b in this embodiment is made of an annular nylon thread having a length of 40 cm.

The positional relationship among the downstream restraint member 87, control spheric body 86 and upstream restraint member 84 is determined so that the control spheric body 86 comes in contact with the upstream restraint member 84 when the intravesical pressure exerted on the upstream side of the control spheric body 86 becomes the second value P2 or less. That is, when the intravesical pressure exceeds the second value P2, the control spheric body 86 is in contact with the downstream restraint member 87, while the control spheric body 86 is apart from the downstream restraint member 87 by the magnetic attractive force of the magnet 85 and comes in contact with the upstream restraint member 84 when the intravesical pressure falls below the second value P2 (i.e. it becomes the second value P2 or less). As the distance L between the upstream restraint member 84 and the downstream restraint member 87, the second value P2 of the pressure becomes small. This is because, even if the pressure exerted on the control spheric body 86 from the upstream side is low, the control spheric body 86 is hardly attracted in the direction toward the upstream restraint member in the case of the large distance L in the state of bringing the control spheric body 86 into contact with the downstream restrainer 87, since the magnetic force acting between the control spheric body 86 and the magnet 85 is inversely proportional to the distance L therebetween. Also, the magnetic strength acting between the control spheric body 86 and the magnet 85 depends on the second value P2 of the pressure. The second value P2 of the pressure is chosen from a value in the range of 1.0 to 50 cmH$_2$O, not exceeding the first value P1 at which the aforementioned upstream restraint member 84 and the control spheric body 86 are separated from each other, and that is the intravesical pressure when closing the urethra at the end of urination. The second value P2 is preferable 20 to 30 cmH$_2$O, and 25 cmH$_2$O or lower in this embodiment.

The restrainer 92 has two wing elements 92a which expand in the horizontal direction from the conduit 83. The upstream member 83a has a U-shaped notch 88 in its end portion on the upstream side of the urethra so as to make it easy to fold the wing elements 92a.

The shape-memory alloy of the deformation part 94 has the transformation temperature lower than the temperature of the urinary bladder. Thus, the shape-memory alloy is kept in a memorized steady shape at the transformation temperature or higher and softly deforms at a temperature lower than the transformation temperature to be deformable freely. In this embodiment, the deformation part is kept in the memorized steady shape at the transformation temperature or higher and softens to be deformable at a lower temperature. The transformation temperature of the shape-memory alloy is desirably determined to 32 to 37° C. in consideration of the temperature of the urinary bladder. To be more specific, the deformation part 94 is formed of thin wires each having a diameter of 0.3 mm so as to become rigid at the transformation temperature of 35° C. or lower while being kept in its memorized L shape and soften to be deformable at a temperature lower than the transformation temperature, e.g. 24° C. or lower. The three thin wires constituting the deformation part 94 are respectively fitted in three grooves 92b extending in the longitudinal direction of the wing element 92a and secured at the lower end portion of the upstream member 83a in such a state of passing through the inside of the upstream member 83a and being inserted into the acrylic intrusion portion 89 having a diameter somewhat smaller than the upstream member 83a.

The urination control device 80 has the conduit 83 inserted in a sheath 91 before setting. The sheath 91 is made of a flexible plastic tube having an inner diameter somewhat larger than the outer diameter of the conduit 83. In the example shown in FIG. 7, the sheath 91 has an inner diameter of 18 to 24 Fr and a length of 10 to 30 cm. The wing elements 92a of the restrainer 92 are made of flexible silicon rubber so as to be deformable responsive to the shape of the deformation part 94 serving as a center core, while the shape-memory alloy of the restrainer 92 is in its softened state specifically at room temperature of 24° C. or lower, consequently to enable substantially free deformation of the wing elements 92a. Hence, the wing elements 92a of the restrainer 92 are held in the sheath 91 in the folded state aligned linearly relative to the conduit 83.

The operation of the urination control device 80 set inside the body will be described hereinafter. As shown in FIG. 10(a), in a case where the urination control device 80 is set in the urethra, the upstream restraint member 84 and the control spheric body 86 come in contact with each other by the magnetic attractive force acting between the magnet 85 and the control spheric body 86 when the intravesical pressure U1 is low. At this time, the conduit is closed by blocking the through hole 84a of the upstream restraint member 84 and the through hole 85a of the magnet 85 with the control spheric body 86. Since the upper portion of the control spheric body 86 closing the opening is exposed on the upstream side through the through holes 84a and 85a, the intravesical pressure U1 is exerted from the upstream.

The intravesical pressure U1 is increased as urine accumulates in the urinary bladder.

When accumulating urine in the urinary bladder with being associated with a desire to urinate, a wearer consciously increases his or her own abdominal pressure. Consequently, when the intravesical pressure U1 comes to the aforementioned first value P1 or more, the control spheric body 86 is disengaged from the upstream restraint member 84 as shown in FIG. 10(b). The disengaged control spheric body 86 is pressed against the downstream restraint member 87 by the urinary flow pressure, coming in fit contact with the member 87. Even if the upstream restraint member 84 ceases closing and the control spheric body 86 is in contact with the downstream restraint member 87, a flow of fluid is allowed to cause urinary flow F, thereby to make urination possible via the conduit 83.

The urinary flow pressure U2 is reduced with progression of the urination. As the flow pressure U2 of the urinary flow F is decreased to the aforementioned second value P2 or lower, the control spheric body 86 comes again in contact with the upstream restraint member 84 while the magnetic force acting between the control spheric body 86 and the magnet 85 resists the flow pressure U3, consequently to close the conduit 83, as shown in FIG. 10(c). Although the urine flow depends on the diameter of the conduit 83 opening in the urinary bladder by the urination control device 80, it is adjusted to 12 to 15 ml/sec., in this embodiment of the invention.

A method of setting the urination control device 80 in this embodiment will be described hereinafter. First, the operation of the restrainer 92 will be explained with reference to FIG. 7 and FIG. 11. In the urination control device 80 at room temperature, the restrainer 92 is in its folded state as shown in FIG. 7. As shown in FIG. 11, the deformation part 94 assumes its memorized shape, i.e. L shape, of the shape-memory alloy when setting the urination control device 80 at a temperature of the transformation temperature or lower, which exceeds 35° C. in this embodiment, upon removing the sheath 91. At this time, the wing elements 92a made of silicon rubber is deformed responsive to the shape of the deformation part 94 serving as a center core, thus to spread the restrainer 92.

When setting the urination control device 80 in the urethra, the deformation part 94 is first softened sufficiently at the transformation temperature or lower, and then, the state in which the wing elements 92a are deformable is confirmed. Incidentally, when the room temperature is 24° C. or higher, the urination control device 80 may be preliminarily cooled before setting in the urethra. Subsequently, the urination control device 80 is thrust into the urethra to be settled in position. At this time, by pushing any part of the conduit 83 with a push stick having a diameter smaller than that of the sheath 91, and on the opposite side, pulling the conduit with the retaining thread 87b, the setting location can be adjusted. Further, the setting location is adjusted by thrusting the urination control device 80 close to the urinary bladder upon inserting the sheath 91 into the urethra 12 so as to bring the upper end of the conduit 83 close to the meatus urethra 12a of the urinary bladder being the bladder sphincter. Thereafter, by removing the sheath 91, the urination control device 80 is retained in position in the urinary bladder as shown in FIG. 12.

As shown in FIG. 13, the urination control device 80 set in the urinary bladder is heated gently by body heat, consequently to spread the restrainer 92 in the opening direction E. Subsequently, the urination control device 80 is brought into contact with the meatus urethra 12a by the spread restrainer 92 by pulling the thread 87b, and then, the steady setting of the urination control device 80 in the urethra is confirmed by getting a feel for a resistance sensation on the thread. In this way, the device can safely and easily be set in position in the urethra without harming the urinary bladder and urethra of the patient. The retaining thread 87b is cut to be removed after setting the device.

The retained urination control device 80 may be adjusted in the meatus urethra of the urinary bladder in the following way. The urination control device 80 can be retained in position on the bladder sphincter close to the meatus urethra by pushing the conduit 83 into the urinary bladder with a push stick in the meantime, pulling the retaining thread 87b after spreading the restrainer 92 to bring the wing elements 92a into contact with the meatus urethra 12a so as to lead the urination control device 80 to the prescribed position.

Next, the method for removing the urination control device 80 in this embodiment will be described. Removing of the urination control device 80 is performed by using a cystoscope with a flexible tube for endoscopically observing, grasping and injecting a liquid. Cooling water with a temperature of 24° C. or lower is preliminarily injected into the urination control device 80 and the urinary bladder by using the cystoscope. Upon confirming that the wing elements 92a having the deformation part 94 as a center core is softened by cooling, the urination control device 80 is pulled out of the urethra 12 while grasping the threading hole 87a by the cystoscope. Since the wing elements 92a are softened to be flexible, they are flexibly deformed in the closing direction C along the urinary bladder and the urethra of the patient. Thus, the urination control device 80 can easily be removed encountering no resistance without harming the urethra and the urethra.

As the urination control device 80 set inside the body is kept at a temperature of a normal body temperature 35° C. or higher, the deformation part 94 assumes the memorized L shape to retain the urination control device 80 in position close to the meatus urethra 12a. A patient who causes an atreturethria ability for the bladder sphincter to diminish due to any disorder or aftereffects is threatened with deterioration in ability of retaining the urination control device 80 in position close to the meatus urethra 12a. Therefore, means for preventing the urination control device 80 from flowing down into the urethra by the pressure of urine is required for such a patient. The urination control device 80 is retained in position close to the meatus urethra 12a by using the restrainer 92 as long as the temperature is maintained at body temperature. Further, the restrainer 92 is softened only by using means for cooling the urination control device 80, consequently to enable easy and safe attaching and removing.

Modified Embodiment

The control member may be formed in not merely the shape like the control spheric bodies 16 and 86 but also any other shape such as a disc shape and conical shape as long as the upstream restraint member can be closed. The upstream restraint member 84 in the third embodiment may be used as a contact spacer in the first and second embodiment and can be adjusted in contact strength by the magnet force acting between the magnet and the control member. The downstream restraint member is provided with a magnet having magnetic force weaker than the magnetic force produced by any of the magnets 15, 65 and 85, so that degree of pressure caused by bringing the control member into contact with the upstream restraint member can be increased to adjust the pressure for urinating.

While the embodiments and modified embodiment according to the invention have been explained with reference to the illustrations, the invention is not limited to the representative device and methods as described. Those of ordinary skill in the art will recognize various modifications which may be made to the embodiments described herein without departing from the scope of the invention.

Industrial Applicability

The urination control device capable of doping with male and female patients representatively with urinary incontinence as aftereffect caused in an operation of radical prostatectomy for carcinoma prostate occurring in men and age-related urinary incontinence requires no surgical operation for being attached and removed relative to the body of the patient and can easily be used extensively for men and women with relieving discomfort due to botheration in using a napkin or handling a utensil for disposing of urine and an objectionable odor, thereby to enable self-sustainability of person who require nursing care, assistant for improving QOL and alleviation of labor for the purpose of dealing with urinary incontinence of person who need nursing care and grow in number in an aging society, thus holding the possibility of coming into wide use to make a contribution to society.

EXPLANATION OF REFERENCE NUMERALS 10, 60, 80 Urination control device
12 Urethra
12a Meatus urethra
13, 83 Conduit
13a, 83a Upstream member
13b, 83b Downstream member
14, 64, 84 Upstream restraint member
14a, 64a, 84a, 85a Through hole
15, 65, 85 Magnet
16, 86 Control spheric body
17, 67, 87 Downstream restraint member
17a, 67a, 87d Fluid pathway hole
17b Bottom
17c Removable part
21, 91 Sheath
22, 92 Restrainer
22a, 92a Wing element
22b Urination passage
23, 73 Removing tool
23a, 73a Attaching/removing structure
23b Push rod
24 Deformation part
67b Engaging hole
73b Rear end
87a Threading hole
87b Retaining thread
87c Protrusion
88 Notch
89 Intrusion portion
C Closing direction
E Opening direction
F Urinary flow
L Distance
P Pushing direction
Q Removing direction
U1, U2, U3 Urinary flow pressure

The invention claimed is:

1. A urination control device comprising:
a conduit configured to be inserted into a urethra;
an upstream restraint member located in said conduit and having a through hole;
a control member located downstream with respect to a flow of urine from a bladder, of said upstream restraint member in said conduit; and
a downstream restraint member located downstream with respect to the flow of urine from the bladder, of said control member in said conduit,
wherein said upstream restraint member is provided with a magnet and said control member is made of a magnetic material so that said upstream restraint member and said control member attract each other by means of magnetic force from said magnet,
wherein said control member is adapted to be brought into contact with or part from said upstream restraint member responsive to an attracted force due to the magnetic force and a fluid pressure on an upstream side with respect to the flow of urine from the bladder, of said control member, and
wherein said control member and said magnet are adapted that said control member parts from an opening portion of said through hole in said upstream restraint member and is brought into contact with said downstream restraint member to allow passage of a fluid through said through hole so as to open said conduit when the fluid pressure on the upstream side with respect to the flow of urine from the bladder, of said control member becomes no less than a first value that is determined by at least said attracted force, and that said control member is brought into contact with said opening portion to block passage of the fluid through said through hole so as to close said conduit when said fluid pressure becomes no more than a second value that is less than said first value.

2. The urination control device according to claim 1, wherein said control member is made of a control spheric body having a diameter larger than an inner diameter of said through hole in said upstream restraint member formed in an annular shape.

3. The urination control device according to claim 1, wherein said downstream restraint member is formed of porous material or wire mesh material so as to allow a flow of the fluid in a state of retaining the control member.

4. The urination control device according to claim 1, wherein said control member is provided on its surface with a metallic film containing Au, Ag, Zn or Sn having a sterilization effect.

5. A urination control device according to claim 1, wherein said first value is selected from the range of 25 to 200 $cmH_2O$ and said second value is selected from a range of 1.0 to 50 $cmH_2O$.

6. The urination control device according to claim 1, wherein said first value is selected from a range of 100 to 180 $cmH_2O$.

7. The urination control device according to claim 1, wherein said second value is selected from a range of 20 to 30 $cmH_2O$.

8. The urination control device according to claim 1, further comprising a support member with a deformation part made of a shape-memory alloy having a transformation temperature lower than a temperature of a urinary bladder on the upstream side of said conduit so as to be held in the urethra by spreading said support member in the urinary bladder.

9. The urination control device according to claim 8, wherein said support member comprises two wing elements which expand auricularly from said conduit, and wherein said deformation part is shaped in a linear shape along said two wing elements and forms an L-shaped axial cross-section at a temperature higher than the temperature of the urinary bladder to spread said two wing elements of said support member in the urinary bladder.

10. The urination control device according to claim 8, wherein said support member is made of a shape-memory alloy having a transformation temperature of 32 to 37° C.

* * * * *